US00H002194H

(19) United States

(12) Statutory Invention Registration

Lund et al.

(10) Reg. No.: US H2194 H

(43) Published: Jul. 3, 2007

(54) PURIFICATION OF PHENOLS

(75) Inventors: Grant James Lund, Johannesburg (ZA); Edward John Coogan, Roodepoort (ZA); Wilhelmina Jansen, Vanderbiljpark (ZA)

(73) Assignee: Merisol (RSA) (Proprietary) Limited, Rosebank, Johannesburg (ZA)

(21) Appl. No.: 10/811,220

(22) Filed: Mar. 26, 2004

(65) Prior Publication Data

US 2004/0200717 A1 Oct. 14, 2004

(30) Foreign Application Priority Data

Apr. 3, 2003 (ZA) ..... 2003/2619
Apr. 3, 2003 (ZA) ..... 2003/2620
Apr. 3, 2003 (ZA) ..... 2003/2621

(51) Int. Cl.
*B01D 11/00* (2006.01)
*B01D 3/00* (2006.01)

(52) U.S. Cl. ..... 203/43; 203/14; 203/100; 568/913

(58) Field of Classification Search ..... None
See application file for complete search history.

(56) References Cited

U.S. PATENT DOCUMENTS

2004/0200717 A1 * 10/2004 Lund et al. ..... 203/43

* cited by examiner

*Primary Examiner*—Dan Pihulic

(74) *Attorney, Agent, or Firm*—Brinks Hofer Gilson & Lione

(57) ABSTRACT

This invention relates to a process for the purification of phenols in a feedstock containing phenols and neutral oils and/or tar bases. The process includes liquid-liquid extraction of feedstock using a solvent and a counter-solvent, and separating the resulting solvent and counter-solvent layers. Phenols are then recovered from the separated solvent layer, and counter-solvent is recovered form the counter-solvent layer. The process also includes at least one of the following additions steps i) subjecting the separated solvent layer to distillation at atmospheric pressure; ii) subjecting the separated solvent layer to distillation, recovering an organic phase from the overheads product of the distillation step and recycling it to the liquid-liquid extraction step; and iii) recovering solvent from the counter-solvent layer.

3 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

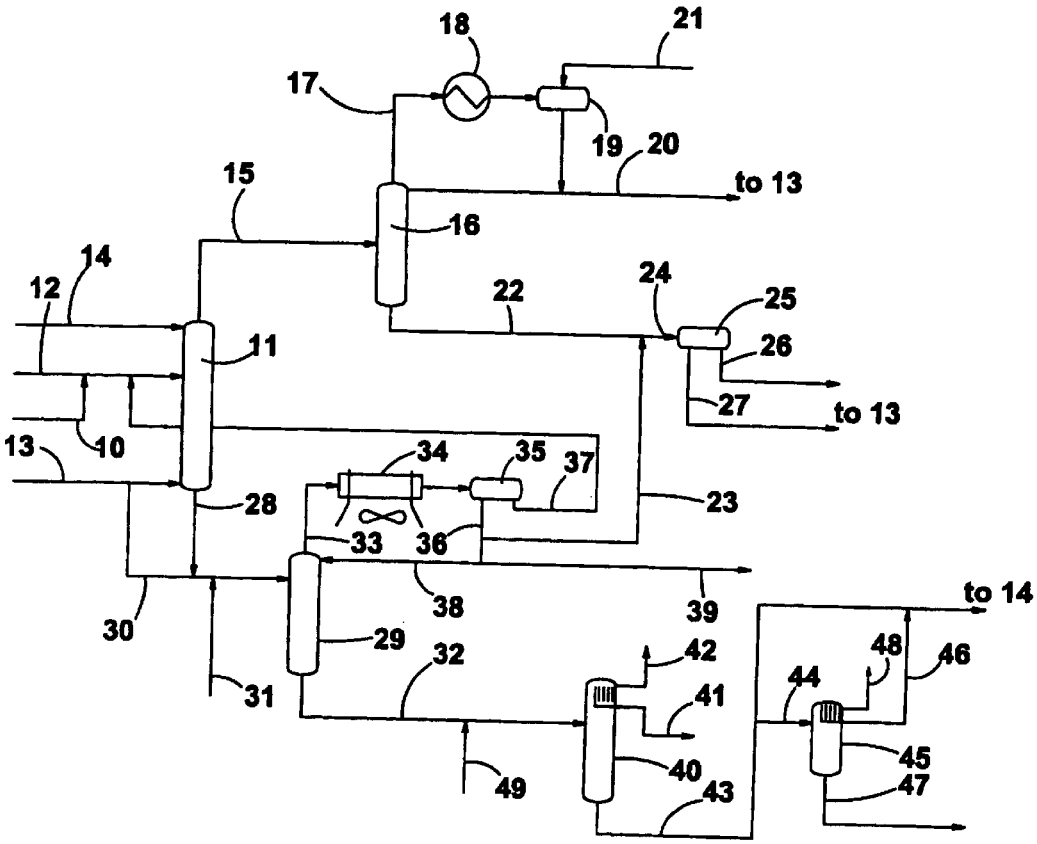
FIGURE

PURIFICATION OF PHENOLS

TECHNICAL FIELD

This invention relates to the purification of phenols in a feedstock containing phenols and neutral oils and/or tar bases.

BACKGROUND ART

Feedstocks containing mixtures of phenols (such as phenol, cresols, ethylphenols, xylenols and C3 phenols) and neutral oils and/or tar bases are obtained from various sources such as petroleum and coal processing facilities.

The separation of phenols from tar bases and especially, neutral oils have always posed a challenge since certain neutral oils have boiling points close to that of the phenols and due to the fact that azeotropes are formed between the neutral oils and phenols. Normal distillation processes are accordingly not suitable to separate phenols from neutral oils and/or tar bases to the required purity.

Liquid-liquid extraction is a known method of separating phenols from neutral oils and/or tar bases. The prior art discloses that both single solvent and dual solvent processes have been employed to achieve such a separation. Dual solvent processes are preferred. In these processes a solvent is used to extract the phenols and a counter-solvent is used to extract the neutral oils. The solvent and counter-solvent are selected to be immiscible and after extraction the solvent and counter-solvent layers are separated and the phenols are recovered from the solvent layer while the neutral oils are recovered from the counter-solvent layer.

The solvent usually is a polar solvent and the counter-solvent usually is a non-polar solvent. The counter-solvent often comprises paraffins such as hexane, heptane, petroleum ether, octane and diesel. The polar solvent often comprises an aqueous solution of methanol, ammonia, acetamide, acetic acid, ethanol and glycols. In this regard see for example U.S. Pat. No. 2,666,796 where aqueous methanol and hexane were used as solvent and counter-solvent respectively. In the Journal of Applied Chemistry, Jun. 21, 1952, p. 314, and the Journal of Applied Chemistry, Mar. 3, 1953, p. 98, aqueous triethylene glycol was used as solvent. In Fuel processing Technology, 28 (1991) p. 287 aqueous solutions of ethylene glycol, diethylene glycol and triethylene glycol were used as solvents. In South African patents 98/11312 and 2001/9287 aqueous solutions of glycols were used as solvents and they were used in combination with counter-solvents.

In cases where the solvent comprises a mixture of water and a solvent compound (e.g. glycols) a solvent layer is obtained which contains the water, the solvent compound (e.g. glycols), phenols, some neutral oils and /or tar bases and some counter-solvent. The first step is usually to subject the mixture to a water recovery distillation process to strip the water from this mixture. The bottoms product consists mainly of the solvent compound (e.g. glycols) and phenols, which bottoms product is then subjected to distillation to separate the phenols from the glycols.

In South African patent 2001/9287 the solvent comprised a mixture of glycol and water and the water recovery distillation process was carried out under vacuum to prevent thermal decomposition of the glycol. The overheads product of the water recovery distillation process (which was now established to consist of water, some counter-solvent, some phenols and some neutral oils and/or tar bases) was condensed and was then mixed with counter-solvent to extract the condensate with the counter-solvent. A decanter was then used to achieve separation of the aqueous and organic layers which formed. It was suggested that the counter-solvent added resulted in extraction of organic material into the counter-solvent layer and it also resulted in better phase separation in the decanter.

One disadvantage of the above system is that the water recovery distillation process is carried out under vacuum. Under such conditions light-boiling valuables such as counter-solvent which enters the water recovery distillation process can be lost to the vacuum system. This is especially problematic where a substantial volume of counter-solvent is present in the water recovery distillation process.

Another disadvantage of this process is that a mixer apparatus is required in order to obtain proper mixing of the condensate of the water recovery distillation process with the introduced counter-solvent to cause proper extraction of the said overheads product.

It is an object of the present invention to overcome or reduce at least some of the above disadvantages.

Furthermore, South African patent 98/11312 discloses a similar water recovery step to that disclosed in South African patent 2001/9287 except that no counter-solvent was added to the overheads product of the water recovery distillation process. In both South African patents 98/11312 and 2001/9287 the separated organic layer from the overheads of the water recovery distillation process was routed to the recovery of the counter-solvent from the counter-solvent layer formed by the liquid-liquid extraction process. In both South African patents 98/11312 and 2001/9287 the counter-solvent recovery was achieved by subjecting the counter-solvent layer to a counter-solvent recovery distillation process to yield recovered counter-solvent (usually as an overheads product) and neutral oils and/or tar bases (usually as a bottoms product). The recovered counter-solvent was then recycled to the liquid-liquid extraction step and the neutral oils and/or tar bases were they routed to a neutral oils and/or tar bases processing facility.

It has now been established that in certain cases the overheads product of the water recovery distillation process contains significant concentration of phenols which form part of the organic layer which is separated from the aqueous layer of the overheads product of the water recovery distillation process (particularly when operating the extract stripper or water recovery distillation under pressure). In the prior art processes of South African patents 98/11312 and 2001/9287 these phenols were lost since they were routed to the counter-solvent recovery process where the phenols ended up with the neutral oils and/or tar bases which were routed to the neutral oils and/or tar bases processing facility.

It is an object of the present invention to at least reduce the above disadvantage.

Furthermore, as stated above in respect of South African patent 2001/19287, after or during the liquid-liquid extraction step the immiscible solvent and counter-solvent layers are separated from each other and the phenols are recovered from the solvent layer (as described above) while the neutral oils and/or nitrogen bases are recovered from the counter-solvent layer. In South African patents 98/11312 and 2001/9287 the counter-solvent layer was subjected to a counter-solvent recovery distillation process to yield recovered counter-solvent (as an overheads product) and neutral oils and/or tar bases (as a bottoms product). The recovered counter-solvent was then recycled to the liquid-liquid extraction step and the neutral oils and/or tar bases were then routed to a neutral oils and/or tar bases processing facility. South African patent 98/4165 describes a similar process for recovering the counter-solvent and in that case the neutral oil (as bottom product) was either used as a feedstock for napthalenes or it was combusted for fuel value.

It has now been established that to obtain optimum conditions for optimum separation of phenols from neutral oils during the liquid-liquid extraction the ratio of solvent to counter-solvent is such that some of the solvent is transferred to the counter-solvent layer. During the counter-solvent recovery distillation process the solvent forms part of the bottom product with the neutral oils and/or tar bases. Since the bottoms product was in the past forwarded to a neutral oils and/or tar base processing facility, or was used as a naphtalenes feedstock, or was combusted as fuel, the solvent contained therein was lost to the process.

It is an object of the present invention to reduce the above disadvantage.

DISCLOSURE OF THE INVENTION

According to a first aspect of the present invention, a process for purifying phenols in a feedstock containing phenols, neutral oils and/or tar bases comprises the steps of i) subjecting the feedstock to liquid-liquid extraction using a solvent in the form of a mixture of water and a solvent compound to transfer the phenols into a solvent layer, and using a counter-solvent to transfer the neutral oils and/or tar bases into a counter-solvent layer;

ii) separating the solvent and counter-solvent layers, which separated solvent layer contains some counter-solvent;

iii) subjecting the separated solvent layer of step (ii) to distillation at or above atmospheric pressure to yield a mixture comprising recovered water and counter-solvent as an overheads product and a mixture comprising the solvent compound and phenols as a bottoms product; and iv) recovering phenols form the bottoms product of step iii) to yield a purified phenols product.

Preferably the distillation of step iii) is operated at a pressure above 0 kPag (i.e. above atmospheric pressure), preferably from 0 to 100 kPag, more preferably at about 20 kPag. The distillation of step iii) is preferably carried out at a temperature at which the solvent compound and preferably also the counter-solvent will not decompose. In the case where triethylene glycol is used as a solvent compound the temperature may be from 150 to 207° C. preferably about 195° C. (in the reboiler). The distillation of step iii) is preferably also performed under such conditions in order that the water concentration is larger than 50 wt% throughout the distillation process preferably greater than 70 wt%. A distillation column may be used to perform the distillation and preferably the water concentration is larger than 50 wt%, preferably larger than 70 wt% throughout the distillation column.

Operating the distillation of step iii) under such conditions will result in some water ending up in the bottoms product of the distillation. This water can be separated out, if required, during later processing steps.

In a preferred embodiment of the invention the separated solvent layer of step (ii) is mixed with a counter-solvent for extracting neutral oils and/or tar bases which may be present in the separated solvent layer during or before the distillation of step iii). Preferably the counter-solvent is added to the feed of the distillation of step iii), that is addition to the separated solvent layer prior to the said distillation. Preferably the counter-solvent is added at a mass ratio of 0 to 0.1 to the separated solvent layer fed to the distillation of step iii), preferably at about 0.04.

The counter-solvent and preferably also the solvent compound preferably comprise organic compounds and preferably the overheads product mixture of step iii) is phase separated to form an aqueous phase and an organic phase, which phases are then separated from each other. The phase separation may be achieved by condensation of the overheads product mixture of step iii), which condensate is then settled to cause the phase formation to take place, and which formed phases are then separated, eg. by decanting.

The separated organic phase of the overheads product mixture of step iii) is preferably recycled to the liquid-liquid extraction step. This organic phase will usually contain counter-solvent, neutral oils and/or tar bases and some phenols. By recycling this phase to the liquid-liquid extraction step the phenols and counter-solvent contained therein are not lost. In the prior art processes these phenols were lost.

The separated water phase of the overheads product mixture of step iii) may be purged or recycled.

By operating the distillation of step iii) under atmospheric or higher pressures the disadvantages of vacuum distillation is avoided or at least reduced. Such a vacuum distillation would cause major losses of counter-solvent to the vacuum system used to create the vacuum. It also improved control of the distillation, but it particularly causes improved separation of the organic and aqueous phases in the overheads product condensed mixture (ie. no counter-solvent is required to be added after condensation of the overheads to step iii).

The addition of counter-solvent to the distillation of step iii) also improves recovery of phenols to the said organic phase and overall. It further improves stripping of neutral oils and/or tar bases during the distillation of step iii). Improved capital and operating costs are also achieved.

Recovery of phenols of step iv) may be achieved by distillation, preferably distillation under vacuum. Water usually forms part of the bottoms product mixture of step iii) and at least some of this water ends up in the vacuum system, used to create a vacuum when the phenols are recovered under vacuum according to step iv). The vacuum system is preferably operated in order to ensure that at least 50 wt%, but preferably most of the water is lost to the vacuum system. This assist in drying the phenols.

However, phenols will also be lost to the vacuum system, but this loss can be minimized by recycling water with phenols therein recovered from the vacuum system, for example, to the distillation of step iii). The water recovered from the vacuum system may be recycled to the feed stream to the distillation of step iii).

The separated counter-solvent layer of step ii) may be subjected to separation of the counter-solvent and the neutral oils and/or tar bases. The counter-solvent and neutral oils and/or tar bases may be separated by distillation, preferably by distillation under pressure. Preferably the counter-solvent is selected to be light boiling relative to the neutral oils and/or tar bases and thus the counter-solvent goes to the overheads product during separation by distillation. The recovered counter-solvent may be recycled to the liquid-liquid extraction step.

The counter-solvent layer of step ii) will usually contain at least some solvent compound (usually due to the solubility of the solvent compound in the counter-solvent) and it will usually also contain some phenols. Although the amount of solvent in the separated counter-solvent layer of step ii) can be adjusted by adjusting operation conditions of the liquid-liquid extraction, such adjustments impact on the effectiveness of the liquid-liquid extraction. The solvent in the separated counter-solvent layer will end up in the bottoms product with the neutral oils and/or tar bases if distillation is used to separate the counter-solvent from the counter-solvent layer. In the prior art such solvent was lost. However, this bottoms product may now be treated to separate the solvent from the neutral oils and/or tar bases. Preferably the said bottoms product from the counter-solvent distillation separation is mixed with water, which mixture is then subjected to phase separation to obtain an organic phase containing the neutral oils and/or tar bases and an aqueous phase containing the water and some solvent compound and usually also some phenols. The aqueous phase may then be recycled to the liquid-liquid extraction step, preferably by adding it to the solvent to be added to the liquid-liquid extraction step. The phase separation may be achieved by a liquid-liquid extraction unit, but preferably the mixture of phases is allowed to settle causing phase separation, which phases are then separated, for example, de-canted.

The water which is mixed to the bottoms product may be fresh clean water or preferably recycled water from overheads of the distillation of step iii). The amount of water to be added should be between 0 to 2 mass ration (with reference to the bottoms product flow rate from the counter-solvent separation), preferably 0.4 mass ratio.

The liquid-liquid extraction may comprise counter-current liquid-liquid extraction and fractional liquid-liquid extraction may be used.

The solvent may comprise a mixture of water and polar solvent, preferably a glycol. Preferably the glycol comprises triethylene glycol (TEG). The mass ratio of water to glycol may be from 0.1 to 0.3. preferably it is about 0.2. The mass ratio of solvent mixture to feedstock may be from 0.3 to 3, preferably about 0.7.

The counter-solvent may comprise a non-polar compound, preferably it comprises a paraffinic compound or a mixture of light paraffinic compounds (e.g. paraffins and isoparaffins). In one embodiment of the invention the counter-solvent may comprise hexane. The mass ratio of counter-solvent to feedstock may be from 0.5 to 3, preferably about 1.8.

Preferably the counter-solvent is low boiling relative to the neutral oils and/or tar bases, and preferably the solvent is high boiling relative to the neutral oils and/or tar bases.

The phase separation of step ii) may be achieved by any convenient manner e.g. decanting or during fractional extraction.

According to a second aspect of the present invention a process for purifying phenols from a feedstock containing phenols, neutral oils and/or tar bases comprises the steps of i) subjecting the feedstock to liquid-liquid extraction using a solvent in the form of mixture of water and a solvent compound to transfer the phenols into a solvent layer, and using an organic counter-solvent to transfer the neutral oils and/or tar bases into a counter-solvent layer;

ii) separating the solvent and counter-solvent layers, the solvent layer optionally containing some counter-solvent;

iii) subjecting the separated solvent layer of step ii) to distillation to yield a mixture comprising recovered water, some phenols and optionally some counter-solvent and some phenols as an overheads product, and a mixture comprising the solvent compound and a major portion of the phenols as a bottoms product;

iv) settling the overheads product of step iii) to form an aqueous phase and an organic phase and separating the phases from each other;

v) recycling the organic phase of step iv) to the liquid-liquid extraction of step i); and vi) recovering the phenols from the bottoms product of step iii) to yield a purified phenols product.

Preferably the distillation of step iii) is operated at or above atmospheric pressure.

According to a third aspect of the present invention the present invention a process for purifying phenols from a feedstock containing phenols, neutral oils and/or tar bases comprises the steps of i) subjecting the feedstock to liquid-liquid extraction using a solvent compound to transfer the phenols into a solvent layer and using a counter-solvent to transfer the neutral oils and/or nitrogen tar bases and at least some solvent compound into a counter-solvent layer;

ii) separating the solvent and counter-solvent layers which separated counter-solvent layer containing some solvent compound;

iii) recovering the counter-solvent from the counter-solvent layer to yield recovered counter-solvent as well as a mixture of solvent compound and neutral oils and/or tar bases;

iv) separating the solvent compound from the neutral oils and/or tar bases from the mixture of solvent compound and neutral oils and/or tar bases obtained in step iii); and v) recovering phenols from the separated solvent layer of step ii) to yield a purified phenols product.

Recovery of the counter-solvent in step iii) may be by means of distillation, preferably by distillation under pressure. Preferably the counter-solvent is selected to be light boiling relative to the neutral oils and/or tar bases and thus the counter-solvent goes to the overheads product during separation by distillation. The recovered counter-solvent may be recycled to the liquid-liquid extraction step.

The counter-solvent layer of step ii) will contain at least some solvent compound (usually due to the solubility of the solvent compound in the counter-solvent) and it will usually also contain some phenols. Although the amount of solvent in the separated counter-solvent layer of step ii) can be adjust by adjusting operation conditions of the liquid-liquid extraction, such adjustments impact on the effectiveness of the liquid-liquid extraction. The solvent (and possibly some of the phenols) in the separated counter-solvent layer will end up in the bottoms product with the neutral oils and/or tar bases if distillation is used to separate the counter-solvent from the counter-solvent layer. In the prior art such solvent and phenols were lost. However, this bottoms product is not treated to separate the solvent and possibly some phenols from the neutral oils and/or tar bases.

In a preferred embodiment of the invention the separation of the solvent compound in step iv) is achieved by extracting the solvent compound from the mixture of solvent and neutral oil and/or tar bases by means of an extraction compound. The extraction compound may comprise a liquid, and preferably it comprises water. The water may comprise water not generated during the process; or water recycled from a process step of the process for purifying phenols from a feedstock. The extraction compound may be mixed with the mixture of solvent compound and neutral oils and/or tar bases obtained in step iii) to extract the solvent compound. This mixture may be subjected to phase separation to obtain an organic phase containing the neutral oils and/or tar nitrogen bases and an aqueous phase containing the water and some solvent compound and usually also some phenols. The aqueous phase may then be recycled to the liquid-liquid extraction step, preferably by adding it to the solvent to be added to the liquid-liquid extraction step. The phase separation may be achieved by a liquid-liquid extraction unit, but preferably the mixture of phases is allowed to settle causing phase separation, which phases are then separated, for example, decanted.

In a preferred embodiment of the invention the solvent compound used in step (i) may form part of a solvent in the form mixture of water and the solvent compound, and at least some of the solvent compound being transferred to the counter-solvent layer while the rest of the solvent compound with at least some water and some counter-solvent is transferred into the solvent layer. In this scenario the phenols may be recovered from the solvent layer by separating the water and counter-solvent as one product from the solvent layer to yield recovered water as well as a mixture of solvent compound and phenols as another product; and thereafter separating the phenols from the solvent compound.

The invention also relates to phenols purified according to any one of the processes as set out above.

The invention will now be further described by means of the attached FIGUER which is a diagrammatic layout of a process according to the invention.

Referring now to the FIGURE a process of purifying phenols in a feedstock stream 10 containing phenols, neutral oils and tar bases comprises as a first step subjecting the feedstock stream 10 to liquid-liquid extraction (LLE) in a liquid-liquid extraction unit 11. The feedstock stream 10 was a concentrated phenols mixed feed stream comprising 90 wt % phenols, the remainder being neutral oils and nitrogen bases in the naphtha/medium creosote range. This feedstock stream 10 was mixed with a feed stream of naphtha 12 having a phenols content of ca. 31 wt % at a mass ratio of 0.3 to the feed stream 11. The concentrated phenols stream (feed stream 10) is cleaned up in the process while the dilute phenols stream (feed stream 12) allows for the production of additional phenols.

Counter-solvent in the form of hexane was fed via stream 13 to the bottom of the LLE unit 11 at a mass ratio of 1.8 to the combined feed streams 10 and 12. Other non-polar counter-solvents in the form of paraffinic compounds or mixtures thereof may be used in other applications. Solvent in the form of a mixture of water and a solvent compound in the form of triethylene glycol (TEG) in a mass ratio of 0.2 water/0.8 TEG. was fed via stream 14 to the LLE unit 11 at the top thereof. The solvent feed 14 was fed at a mass ratio of 0.7 to the combined feeds 10 and 12. Other polar solvents, especially aqueous polar solvents may be used in other cases.

The LLE unit 11 can be any conventional LLE unit (e.g. packed, Karr, rotating disc contactor), but in this case it was a Scheibel type counter-current unit. The impeller diameter of the unit 11 was different throughout the length of the column to maximize mass transfer and throughput before flooding commences. The LLE unit 11 may be operated at various temperature (e.g. 25 to 70° C.) but in this particular example it was operated at a temperature of 45° C.

The raffinate stream 15 of the LLE unit 11 contained counter-solvent, and smaller amounts of phenols and TEG (due to its solubility in the counter-solvent). The raffinate stream 15 was fed to a distillation column (or rafinate stripper) 16 to recover the counter-solvent as an overheads product stream 17 which was condensed in a condenser 18 and transferred to a reflux drum 19. The recovered counter-solvent was recycled via stream 20 to the LLE unit 11, particularly to feed stream 13. Counter-solvent make up may be added via stream 21 to the reflux drum 19 as this gives a quick response to surges. Alternatively [not shown], counter-solvent make-up may be added to the counter-solvent feed stream 13. The distillation column 16 may be run at 0–200 kPag pressure and a temperature profile from 55 to 230° C. In this example the pressure was 70 kPag and the reboiler temperature was 215° C.

The bottoms product stream 22 of the distillation column 16 was rich in neutral oils and tar bases, but also included some TEG and some phenols. This bottoms product stream 22 was mixed with water at a ratio of 0.4, which water was from stream 23 (which will be described later). The resultant mixture stream 24 was fed to a decanter 25 where it phase separated into an organic layer stream 26 of neutral oils and tar bases which was further worked up [not shown]; and an aqueous layer stream 27 containing water and recovered TEG and some recovered phenols. The stream 27 was recycled to the LLE unit 11, particularly to the solvent feed stream 14. The one main advantage of addition of water via stream 23 and the separation in 25 is that TEG is recovered, which is then recycled. The use of water via stream 23 also minimizes the water balance (i.e. purging of water). In the decanter 25 the temperature was 55° C. and the pressure was 15 kPag, but other temperature e.g. 25 to 75° C. and other pressures may also be used.

The bottoms stream 28 from the LLE unit 11 mainly comprised solvent compound (TEG), water, phenols, some counter-solvent and some neutral oils and tar bases. The stream 28 was fed to a distillation column or extract stripper 29 and it was mixed with a slipstream 30 of counter-solvent and a stream 31 waste water from a vacuum system, in particular steam ejectors (not shown, but described later) at a mass ration of 0.04 counter solvent and 0.04 water from ejectors to total feed to extract stripper 29. The extract stripper 29 was operated under pressure, namely a pressure of 30 kPag. Some water was removed with the solvent compound (TEG) and phenols via the bottoms stream 32. The water dramatically decreased the reboiler[not shown] temperature which prevented TEG degradation. Although most of the water was removed via the overheads stream 33 (which contained water, some counter-solvent [which was light boiling], some neutral oils and tar bases, and some azeotroped phenols) the unit 29 no longer operated as a pure water recovery unit but as an extract stripper as it stripped the remaining neutral oils or tar bases from the phenols and the solvent compound.

The overheads stream 33 was condensed by means of the condenser 34 and the condensate was then phase separated in the reflux drum/decanter 35 into an aqueous layer stream 36 and an organic layer stream 37. The aqueous layer stream 36 was essentially free of phenols, neutral oils and tar bases and was partly fed via stream 38 as reflux to the stripper 29. Some of the remaining water, that is in stream 39, was worked up and some of this was purged to close the water mass balance, while some water, that is in stream 23, was mixed with the stream 22 as described above.

The organic layer stream 37 comprised counter-solvent, phenols, neutral oils, and tar bases and was recycled to the LLE unit 11, particularly to the naphtha feed stream 12. (Ratio ca. 0.2:1 (mass)). Alternatively it may be added to the counter-solvent feed stream 13 or the solvent feed stream 14, but the latter is not suggested. Since the stripper 29 was operated under pressure measurable amounts of phenols were lost to the overheads stream 33, but it was not lost to the process as it was recycled to the LLE unit 11 via stream 37.

Addition of the counter-solvent via stream 30 to the bottoms stream 28 prior to the stripper 29 improved phase separation in the decanter 35. Running the stripper 29 under pressure allowed for addition of counter-solvent to the stripper 29 without loss of the counter-solvent to a vacuum system (as in the prior art). More phenols were removed overhead via stream 33 but it was recovered via the recycling of the organic layer stream 37. Pressure operation of the stripper 29 gave more control to the stripper 29 and allowed for improved operation of the reflux drum/decanter 35.

The bottoms stream 32 contained solvent compound (TEG), phenols and some water and was forwarded to a distillation column or product stripper 40 which operated under vacuum to strip the phenols as an overheads stream 41. The vacuum system [not shown] was run to ensure that at least 50 wt%, but preferably more water was lost to the vacuum system via stream 42. Dirty solvent product was recovered as the bottoms stream 43. The unit 40 was operated under vacuum because of the solvent compound (TEG) degradation temperature and the stream saturation temperature. Typically the operating pressure is 3,5 kPa abs and typically the bottoms temperature <195° C., usually about 195° C.

The dirty solvent stream 43 was recycled back to LLE unit 11 especially to the solvent feed stream 14. A small slip stream 44 was cleaned by means of flash evaporation in the unit 45. The clean solvent stream 46 was mixed with the dirty solvent stream 43. The bottoms product stream 47 was removed to be processed further. The flash evaporation 45 was typically run at 2 kPa abs and at a temperature of 167° C.

The vent 48 of the flash was recovered in the vacuum system [not shown] which was recovered as a waste water stream 31, which was returned to the stripper 29.

The addition of the waste water stream 31 from the vacuum system of unit 40 means that phenols lost to the vacuum system may be recovered in the stripper 29. The waste water stream 31 may be added to the reflux drum/decanter 35 but it is not recommended as it may contain solvent which will be purged via the stream 39.

Make up TEG can be added as stream 49.

The separated phenols of stream 41 had a composition of 95%+phenols, and ca. 1.6 wt% water. If required the water may be removed in a subsequent step by means of for example a distillation unit.

It will be appreciated that many variations in detail are possible without thereby departing from the scope and spirit of the invention.

What is claimed is:

1. A process for purifying phenols in a feedstock containing phenols, neutral oils and/or tar bases comprising the steps of i) subjecting the feedstock to liquid-liquid extraction using a solvent in the form of a mixture of water and a solvent compound to transfer the phenols into a solvent layer, and using a counter-solvent to transfer the neutral oils and/or tar bases into a counter-solvent layer;

ii) separating the solvent and counter-solvent layers, which separated solvent layer contains some counter-solvent;

iii) subjecting the separated solvent layer of step (ii) to distillation at or above atmospheric pressure to yield a mixture comprising recovered water and counter-solvent as an overheads product and a mixture comprising the solvent compound and phenols as a bottoms product; and iv) recovering phenols from the bottoms product of step iii) to yield a purified phenols product.

2. A process for purifying phenols from a feedstock containing phenols, neutral oils and/or tar bases comprising the steps of i) subjecting the feedstock to liquid-liquid extraction using a solvent in the form of mixture of water and a solvent compound to transfer the phenols into a solvent layer, and using an organic counter-solvent to transfer the neutral oils and/or tar bases into a counter-solvent layer;

ii) separating the solvent and counter-solvent layers, the solvent layer optionally containing some counter-solvent;

iii) subjecting the separated solvent layer of step ii) to distillation to yield a mixture comprising recovered water, some phenols and optionally some counter-solvent as an overheads product, and a mixture comprising the solvent compound and a major portion of the phenols as a bottoms product;

iv) settling the overheads product of step iii) to form an aqueous phase and an organic phase and separating the phases from each other;

v) recycling the organic phase of step iv) to the liquid-liquid extraction of step i); and vi) recovering the phenols from the bottoms product of step iii) to yield a purified phenols product.

3. A process for purifying phenols from a feedstock containing phenols, neutral oils and/or tar bases comprising the steps of i) subjecting the feedstock to liquid-liquid extraction using a solvent compound to transfer the phenols into a solvent layer and using a counter-solvent to transfer the neutral oils and/or tar bases and some solvent compound into a counter-solvent layer;

ii) separating the solvent and counter-solvent layers, which separated counter-solvent layer contains some solvent compound;

iii) recovering the counter-solvent from the separated counter-solvent layer to yield recovered counter-solvent as well as a mixture of solvent compound and neutral oils and/or tar bases;

iv) separating the solvent compound from the neutral oils and/or tar bases from the mixture of solvent compound and neutral oils and/or tar bases obtained in step iii); and v) recovering phenols from the separated solvent layer of step ii) to yield a purified phenols product.

* * * * *